United States Patent [19]

Herwig et al.

[11] 4,371,725

[45] Feb. 1, 1983

[54] PROCESS FOR THE PREPARATION OF TERTIARY OLEFINS AND N-ALKANOLS

[75] Inventors: Jens Herwig, Cologne; Bernhard Schleppinghoff; Hans-Volker Scheef, both of Dormagen, all of Fed. Rep. of Germany

[73] Assignee: EC Erdolchemie GmbH, Cologne, Fed. Rep. of Germany

[21] Appl. No.: 326,646

[22] Filed: Dec. 2, 1981

[30] Foreign Application Priority Data

Dec. 19, 1980 [DE] Fed. Rep. of Germany ....... 3048084

[51] Int. Cl.$^3$ .................... C07C 29/00; C07C 1/20
[52] U.S. Cl. ..................................... 568/907; 585/639
[58] Field of Search .................... 568/907; 585/639

[56] References Cited

U.S. PATENT DOCUMENTS

| 3,170,000 | 2/1965 | Verdol | 568/907 |
| 4,006,198 | 2/1977 | Tesei et al. | 568/907 |
| 4,025,575 | 5/1977 | Chang et al. | 260/682 |
| 4,238,631 | 12/1980 | Daviduk et al. | 585/639 |
| 4,306,106 | 12/1981 | Kerr et al. | 585/639 |

*Primary Examiner*—Joseph E. Evans
*Attorney, Agent, or Firm*—Sprung, Horn, Kramer & Woods

[57] ABSTRACT

Process for the preparation of tertiary olefins by catalytic cleavage of their n-alkyl ethers at elevated temperature and with simultaneously recovery of the corresponding n-alkanols, characterized in that the cleavage is carried out in the presence of acidic molecular sieves, which have been activated, if necessary, by a treatment with hydrogen, at temperatures of from 100° to 300° C.

12 Claims, No Drawings

PROCESS FOR THE PREPARATION OF TERTIARY OLEFINS AND N-ALKANOLS

The present invention relates to a process for the preparation of tertiary olefins by catalytic cleavage of their n-alkyl ethers.

Tertiary olefins are important intermediates for the preparation of polymers and higher grade chemicals. Thus, the interesting function of the double bond at the tertiary carbon atom allows the production of numerous organic intermediate products, such as, for example, pinacolin and neocarboxylic acids, and by dehydrogenation, conjugated diolefins, such as, for example, isoprene, which can be further processed in the plastics, pharmaceutical, plant protection and lubricant sectors. The prerequisite for reactions of this type is the availability of such tertiary olefins in as high a purity as possible.

Since these tertiary olefins occur, in the main, in mixture with other hydrocarbons in the product spectrum of thermal and catalytic crackers, an isolation process must be employed for their purification. The sulphuric acid process has hitherto been the primary means for the isolation of the tertiary olefins from the hydrocarbon streams mentioned, a process in which, firstly, the sulphuric acid esters of the tertiary alcohols corresponding to the tertiary olefins were formed, which were then re-formed to give the tertiary olefins again, by 'splitting off' the sulphuric acid. The problems of this process arise from the unavoidable corrosion and from the necessity for concentrating up the used acid prior to its recycling. In more recent times, processes have been developed which, starting from a selective etherification of the tertiary olefins with alcohols, achieve the purification of the tertiary olefins via the decomposition of these ethers (European Patent Application No. 0,003,305; U.S. Pat. No. 3,170,000 and German Offenlegungsschrift No. 2,924,869. In the cleavage of the tertiary ethers, the formation of the dialkyl ethers from the n-alkanols split off occurs as an undesired side reaction, to an increasing extent with increasing reaction temperature. A particular disadvantage of this ether formation arises from the water formed thereby, which, with an alkanol cycle, must be removed again before the etherification step. Catalysts to decompose the ethers are therefore being sought, the activity of which is great enough to function at low temperatures, or the selectivity of which is high enough to produce as low a formation as possible of ethers. Such a catalyst is described in DE-OS (German Published Specification) No. 2,924,869, in the form of crystalline silicic acid. However, in order to achieve as large conversions as possible, it is necessary, even with this catalyst, to work at the relatively high temperature of over 190° C. up to the region of about 350° C.

A process for the preparation of tertiary olefins by catalytic cleavage of their n-alkyl ethers at elevated temperature and with simultaneous recovery of the corresponding n-alkanols has now been found, which is characterised in that the cleavage is carried out in the presence of acidic molecular sieves, which have been activated, if necessary, by a treatment with hydrogen, at temperatures of from 100° to 300° C.

Zeolites, acidic aluminum oxides and H-mordenites may be mentioned as examples of molecular sieves which can be used in the process according to the invention. Zeolites are understood here to mean water-containing silicate frameworks of the general formula $x[(M', M''_{0.5})AlO_2] \cdot y\ SiO_2 \cdot zH_2O$ with $M'=$Li, Na, K etc. and $M''=$Mg, Ca, Sr, Ba, etc. (Fortschr. Mineral 42, 50 (1965)). They usually have a crystalline structure, as determined by X-ray diffraction analysis, and are porous. The pores are usually uniform in size, especially diameter. Furthermore, H-mordenites are understood to mean orthorhombic silicate frameworks of the formula $Na_8[(AlO_2)_8 \cdot (SiO_2)_{40}] \cdot 24H_2O$, the Na atoms of which can be successively exchanged for H atoms (Am. Mineral, 39, 819 (1954)).

H-Mordenites are preferably employed. These molecular sieves which can be used according to the invention are available in their acidic $H^+$ form.

The acidic molecular sieves described can be employed according to the invention individually as well as in a mixture of 2 or more of the molecular sieves mentioned. In the case that the selectivity of the molecular sieve employed according to the invention as catalyst, or of the mixture of several molecular sieves, is to be increased, which, in general, is accompanied by a decrease in the activity and/or a decrease in the throughput, it can be of advantage to mix the molecular sieves used with, for example, 0.01 to 80% by weight, relative to the amount of the molecular sieves, of aluminum oxide and/or amorphous alumosilicates, and to employ the mixture thereby obtained as catalyst. For a specific task within the scope of the present invention, the necessity and, if necessary, the extent of such an admixture can be determined by simple preliminary experiments.

The catalytically active acidic molecular sieves for the process according to the invention have an effective pore volume of, for example, 0.05 to 0.6, preferably 0.12 to 0.3 ml/g. Furthermore, they have an effective pore diameter of, for example, 3 to 15, preferably 7 to 12, particularly preferably 8 to 11 Å. The specific surface area is, for example, 100 to 700, preferably 300 to 550 $m^2/g$. The following molecular sieves are contemplated: X-, Y-, A-, T-zeolite, faujasite, ZSM-5-zeolite, H-mordenite.

The process according to the invention is carried out, for example, at a temperature of 100° to 300° C., preferably 110° to 210° C., particularly preferably 120° to 180° C. The reaction can be carried out in the gas phase as well as in the liquid phase at a pressure of, for example, 0.1 to 50 bar, preferably 1 to 20 bar.

A WHSV (weight-hourly-space-velocity) in the range from 0.5 to 10 g substrate/g catalyst/hour is chosen for the catalyst load.

It has additionally been found that the catalyst for the process according to the invention undergoes an increase in activity on treatment with hydrogen before its employment as catalyst. This activity-increasing hydrogen treatment of the catalyst consisting of one or several of the molecular sieves described above and, if appropriate, of the components, which have been described, of the mixture can take place before its initial employment as well as before a subsequent employment of an already used catalyst. This activity-increasing hydrogen treatment of an already used catalyst can be undertaken if the catalyst shows signs of exhaustion and also as a preventive measure, before signs of exhaustion in the catalyst are detectable. This hydrogen treatment can be carried out, for example, with 50 to 500 liters of hydrogen per liter of catalyst at 100° to 450° C. at 1 to 50 bar for a 1 to 60 hours. This hydrogen treatment can, of course, be carried out in a separate reactor designed for the purpose, but equally well also in the reactor provided for the ether cleavage according to the invention, provided this reactor is equipped for the hydrogen treatment. Thus, for example, still unused catalyst can be poured into the reactor provided for the ether cleavage, the catalyst can be treated with hydrogen under the conditions described, after which the hydrogen used for the treatment is removed, for example by flushing with nitrogen and, by feeding in the ether to be cleaved and adjustment of the conditions according to the invention, the catalyst is brought into use. Furthermore, an already used catalyst can be subjected to the hydrogen treatment without removal from the cleavage reactor by displacing the ether to be cleaved hitherto fed in, for example by means of nitrogen, and the catalyst is then activated by feeding in the desired amount of hydrogen and adjustment of the parameters described for the hydrogen treatment.

n-Alkyl ethers of tertiary olefins for the process according to the invention are, for example, those of the general formula

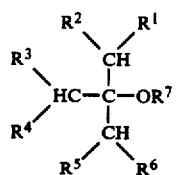
(I)

which are split according to the invention to give tertiary olefins of the general formula

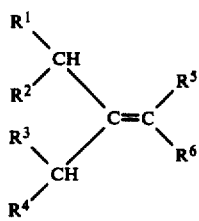
(II)

and n-alkanols of the formula $R^7OH$ (III)

wherein $R^1$ denotes hydrogen or straight-chain or branched alkyl with 1 to 8, preferably 1 to 4, particularly preferably 1 to 2 C atoms, $R^2$ to $R^6$ denote hydrogen or alkyl with 1 to 4, preferably 1 to 2, especially preferably with 1 C atom and $R^7$ denotes straight-chain or branched alkyl with 1 to 6, preferably with 1 to 4, particularly preferably 1 to 2 C atoms.

The following ethers may be mentioned as examples of starting materials of the formula (I) for the process according to the invention: methyl-tert.-butyl ether, ethyl-tert.-butyl ether, propyl-tert.-butyl ether, n-butyl-tert.-butyl ether, n-amyl-tert.-butyl ether, methyl-tert.-amyl ether, ethyl-tert.-amyl ether, propyl-tert.-amyl ether, n-butyl-tert.-amyl ether, n-amyl-tert.-amyl ether, n-hexyl-tert.-amyl ether, methyl-tert.-hexyl ether and ethyl-tert.-hexyl ether.

The products obtainable according to the invention are, in addition to the particular n-alkanols, the tertiary olefines, such as isobutene, isoamylene, isohexene and others.

The purification of the tertiary olefins which can be produced according to the invention is effected in a distillation step downstream from the cleavage reactor, whereby the desired olefines are taken off as a top product in a purity of over 96% by weight and a bottom product accumulates which, having a composition of about 90 to 99.9% by weight of alkanol, 0.1 to 10% by weight of the ether employed and small amounts of water, can be recycled to the process for etherification of the tertiary olefines.

In contrast to the sulphuric acid extraction process for the preparation of tertiary olefins the process according to the invention requires a catalyst without corrosive properties, so that normal carbon steels can be used for the reactor material. The process according to the invention is distinguished, in contrast with the catalytic cleavage process described above, by a higher activity of the catalyst to be used, so that the catalytic cleavage can be carried out at lower temperatures. This lower reaction temperature greatly reduces the portion of undesired di-n-alkyl ether formed of necessity, so that over 90% of the n-alkanol introduced into circulation can be reclaimed, and, as a result of the high activity of the catalyst employed according to the invention, high yields and high throughputs are simultaneously achieved in the cleavage process. At the same time, an energy-saving method of carrying out the reaction results from the lowering of the reaction temperature.

EXAMPLES

A thermostat-controlled continuous reactor was employed as the alkyl ether cleavage reactor. For a given internal reactor radius of 25 mm, the height of the catalyst bed was so chosen that the catalyst charge was 100 g. To monitor the temperature, the reactor was equipped with temperature measuring devices at intervals of 100 mm. The pressure in the reactor was regulated by maintaining an overpressure. The metered addition of the substrate was effected via a diaphragm piston pump. The composition of the reaction product obtained at the exit of the reactor was examined by means of gas chromatography. The product stream was worked up in a downstream distillation column. The desired iso-olefins were obtained thereby as a top product in a purity of over 95% by weight.

The following abbreviations are used: TAME=tert.-amyl-methyl ether; MB=methylbutene; DME=-dimethyl ether; WHSV=weight-hourly-space-velocity; GC=gas chromatography; MW=molecular weight.

In Examples 1–10 the temperature dependence of the ether cleavage has been investigated in connection with the formation of dimethyl ether.

Catalyst: 100 g $H^+$-mordenite

Starting product: 100 g TAME/h (GC 99.9% by weight) (MW 102.2)

Reaction pressure 10 bar; reaction time 6 h;

$$WHSV = 1 \left( \frac{g\ substrate}{g\ catalyst \cdot h} \right)$$

| Example | (No.) | 1 | 2 | 3 | 4 | 5 |
|---|---|---|---|---|---|---|
| Temp. | (°C.) | 120 | 130 | 140 | 160 | 180 |

-continued

| | | | | | | |
|---|---|---|---|---|---|---|
| TAME | weight % | 32.3 | 24.3 | 18.7 | 12.7 | 2.1 |
| 2-MB-2 | " | 34.0 | 37.2 | 41.0 | 44.0 | 53.4 |
| 2-MB-1 | " | 12.5 | 14.8 | 14.8 | 15.9 | 13.8 |
| 3-MB-1 | " | — | — | — | — | — |
| $CH_3OH$ | " | 19.9 | 22.2 | 23.8 | 25.4 | 24.6 |
| DME | " | 0.9 | 1.1 | 1.2 | 1.4 | 4.4 |
| $H_2O$ | " | 0.4 | 0.4 | 0.5 | 0.6 | 1.7 |
| Conversion TAME | % | 67.7 | 75.7 | 81.3 | 87.3 | 97.9 |
| Selectivity $CH_3OH$ | | 93.7 | 93.6 | 93.3 | 92.7 | 80.1 |
| Yield $CH_3OH$ | % | 63.5 | 70.8 | 75.9 | 81.0 | 78.4 |

| Example | (No.) | 6 | 7 | 8 | 9 | 10 |
|---|---|---|---|---|---|---|
| Temp. | (°C.) | 200 | 220 | 250 | 280 | 300 |
| TAME | weight % | 1.2 | 0.9 | 0.4 | 0.2 | 0.2 |
| 2-MB-2 | " | 51.9 | 53.2 | 53.5 | 52.9 | 53.4 |
| 2-MB-1 | " | 15.9 | 14.8 | 14.8 | 15.4 | 14.8 |
| 3-MB-1 | " | 0.1 | 0.1 | 0.1 | 0.2 | 0.3 |
| $CH_3OH$ | " | 24.6 | 24.0 | 23.3 | 18.8 | 17.5 |
| DME | " | 4.5 | 5.0 | 5.7 | 9.0 | 9.9 |
| $H_2O$ | | 1.8 | 2.0 | 2.2 | 3.5 | 3.9 |
| Conversion TAME | % | 98.8 | 99.1 | 99.6 | 99.8 | 99.8 |
| Yield $CH_3OH$ | % | 79.6 | 77.4 | 74.3 | 59.9 | 55.9 |
| Selectivity $CH_3OH$ | | 78.4 | 76.5 | 74.3 | 59.9 | 55.8 |

The preliminary treatment with $H_2$ of the $H^+$-mordenite employed was investigated in Examples 11–13. Data for the preliminary treatment:

| Catalyst: | 100 g $H^+$-mordenite |
|---|---|
| T-preliminary treatment: | 190° C. |
| p-preliminary treatment: | 27 bar |
| t-preliminary treatment: | 24 h |
| $H_2$: | 40 l/h |

After this preliminary treatment, the $H_2$ pressure was released and the reaction pressure adjusted to 10 bar with $N_2$.

The following reaction conditions were fixed: p-reaction = 10 bar; T-reaction = 140° C.; t-reaction = 24 h; WHSV = 1 (g substrate/g catalyst.h) starting material 100 g TAME/h (GC 99.9% by weight).

| Example (No.) | | 11 | 12 | 13 |
|---|---|---|---|---|
| $H_2$ treatment | | (−) | (+) | (+) |
| TAME | weight % | 18.7 | 3.8 | 4.4 |
| 2-MB-2 | " | 41.0 | 49.2 | 48.3 |
| 2-MB-1 | " | 14.8 | 16.8 | 17.3 |
| 3-MB-1 | " | — | — | — |
| $CH_3OH$ | " | 23.8 | 28.0 | 27.4 |
| DME | " | 1.2 | 1.6 | 1.9 |
| $H_2O$ | " | 0.5 | 0.6 | 0.7 |
| Conversion TAME | % | 81.3 | 96.2 | 95.6 |
| Selectivity $CH_3OH$ | % | 93.3 | 92.7 | 91.3 |
| Yield $CH_3OH$ | % | 75.9 | 89.3 | 87.1 |

+ Regeneration of an already used catalyst

The dependence of the ether cleavage on the catalyst load was examined in Examples 14–18. The $H^+$-mordenite employed was subjected to an $H_2$ preliminary treatment analogously to Examples 12 and 13.

| Catalyst: | 100 g $H^+$-mordenite ($H_2$ activated) |
|---|---|
| Starting material: | TAME (99.9% by weight) |

-continued

| Reaction conditions: | p-reaction = 10 bar; T-reaction 140° C.; t-reaction = 6 h |
|---|---|
| Catalyst load: | $\text{WHSV} \left( \dfrac{\text{g substrate}}{\text{g catalyst} \cdot \text{h}} \right)$ 0.5–3.0 |

| Example No. | | 14 | 15 | 16 | 17 | 18 |
|---|---|---|---|---|---|---|
| WHSV | | 0.5 | 1.0 | 1.5 | 2.0 | 3.0 |
| TAME | weight % | 13.4 | 3.8 | 3.6 | 4.0 | 5.2 |
| 2-MB-2 | " | 44.0 | 49.2 | 51.4 | 52.1 | 54.3 |
| 2-MB-1 | " | 15.2 | 16.8 | 14.8 | 13.8 | 10.8 |
| 3-MB-1 | " | — | — | — | — | — |
| $CH_3OH$ | " | 23.5 | 28.0 | 28.0 | 28.2 | 28.8 |
| DME | " | 2.8 | 1.6 | 1.6 | 1.4 | 0.7 |
| $H_2O$ | " | 1.1 | 0.6 | 0.6 | 0.5 | 0.2 |
| Conversion TAME | % | 86.3 | 96.2 | 96.4 | 96.0 | 94.8 |
| Selectivity $CH_3OH$ | % | 85.8 | 92.7 | 92.7 | 93.7 | 97.0 |
| Yield $CH_3OH$ | % | 75.0 | 89.3 | 89.3 | 89.9 | 91.8 |

Various alkyl ethers were examined with respect to their cleavability in the Examples 19 to 20.

The reaction conditions analogous to the TAME cleavage experiments were assumed.

Compounds employed:
MTBE (methyl-tert.-butyl ether), MW 88.2
TAEE (tert.-amyl-ethyl ether), MW 116.2

In the case of MTBE, isobutene and methanol are obtained as the cleavage product.

In the case of TAEE, iso-amylene and ethanol are obtained as the cleavage product.

| Example 19: | |
|---|---|
| Catalyst: | 100 g $H^+$-mordenite ($H_2$ activated) |
| Starting material: | MTBE (99.9% by weight) |
| Reaction conditions: | T-reaction = 140° C. |
| | p-reaction = 10 bar |
| | t-reaction = 6 h |
| Catalyst load: | $\text{WHSV} = 1 \left( \dfrac{\text{g substrate}}{\text{g catalyst} \cdot \text{h}} \right)$ |
| MTBE | weight % | 9.2 |
| i-$C_4$ | " | 57.8 |
| $CH_3OH$ | " | 30.5 |
| DME | " | 1.8 |
| $H_2O$ | " | 0.7 |
| Conversion MTBE | % | 90.8 |
| Selectivity $CH_3OH$ | % | 92.4 |
| Yield $CH_3OH$ | % | 83.9 |

| Example 20: | |
|---|---|
| Catalyst: | 100 g $H^+$-mordenite |
| Starting material: | TAEE (GC 99.9% by weight) |
| Reaction conditions: | T-reaction = 140° C. |
| | p-reaction = 10 bar |
| | t-reaction = 6 h |

-continued

Example 20:

Catalyst load:

$$WHSV = 1 \left( \frac{g\ substrate}{g\ catalyst \cdot h} \right)$$

| | | |
|---|---|---|
| TAEE | weight % | 5.1 |
| 2-MB-2 | " | 42.9 |
| 2-MB-1 | " | 14.3 |
| 3-MB-1 | " | — |
| C$_2$H$_5$OH | " | 34.1 |
| DEE | " | 2.9 |
| H$_2$O | " | 0.7 |
| Conversion | | |
| TAEE | % | 94.9 |
| Selectivity | | |
| C$_2$H$_5$OH | % | 90.5 |
| Yield | % | 85.9 |
| C$_2$H$_5$OH | | |

What is claimed is:

1. A process for preparing a tertiary olefin from the corresponding n-alkyl ether thereof which comprises contacting said n-alkyl ether with hydrogen in the presence of an acidic molecular sieve at a temperature from 100° to 300° C. and simultaneously removing the n-alkanol which forms.

2. A process according to claim 1, wherein said acid molecular sieve is X-, Y-, A-, T-zeolite, faujasite, ZSM-5-zeolite or H-mordenite, especially H-mordenite.

3. A process according to claim 1, wherein said molecular sieve is a molecular sieve having a pore diameter of 3 to 15 angstroms.

4. A process according to claim 3, wherein said molecular sieve has a pore diameter of 7 to 12 angstroms.

5. A process according to claim 4, wherein said molecular sieve has pore diameters of 8 to 11 anstroms.

6. A process according to claim 1, wherein said molecular sieve has a BET surface area of 100 to 700 square meters per gram.

7. A process according to claim 1, wherein said acidic molecular sieve is disposed in an aluminum oxide or alumina silica composition in an amount of 0.01 to 80% by weight.

8. A process according to claim 1, wherein said molecular sieve has an effective pore volume of 0.05 to 0.6 ml/g.

9. A process according to claim 1, wherein the process is carried out at a temperature of 110° to 210° C.

10. A process according to claim 1, wherein the process is carried out at a temperature of 120° to 180° C.

11. A process according to claim 1, wherein the process is carried out while maintaining a catalyst load of from 0.5 to 10 grams substrate per gram catalyst per hour.

12. A process according to claim 1, wherein said acid molecular sieve is one which has been treated with 50 to 500 liters of hydrogen per liter of molecular sieve at 100° to 450° C. at 1 to 50 bars for 1 to 60 hours before employment in the preparation of a tertiary olefin by contacting an n-alkyl ether thereof with said acidic molecular sieve.

* * * * *